United States Patent [19]
Hyatt

[11] Patent Number: 5,670,668
[45] Date of Patent: Sep. 23, 1997

[54] CRYSTALLINE TOCOTRIENOL ESTERS

[75] Inventor: John Anthony Hyatt, Kingsport, Tenn.

[73] Assignee: Eastman Chemical Company, Kingsport, Tenn.

[21] Appl. No.: 674,949

[22] Filed: Jul. 3, 1996

[51] Int. Cl.⁶ ................................ C07D 311/72
[52] U.S. Cl. ................................ 549/410
[58] Field of Search ........................ 549/410

[56] References Cited

U.S. PATENT DOCUMENTS

| | | | |
|---|---|---|---|
| 4,939,276 | 7/1990 | Fixet | 549/413 |
| 5,190,618 | 3/1993 | Top et al. | 203/34 |

FOREIGN PATENT DOCUMENTS 2218989  11/1989  United Kingdom .

OTHER PUBLICATIONS

A. Kato et al., Japanese Kokai SHO 61–93178 (1986).
J. Baxter et al., J. Am. Chem. Soc. 65, 918 (1943).

*Primary Examiner*—Nicky Chan
*Attorney, Agent, or Firm*—J. Frederick Thomsen; Harry J. Gwinnell

[57] ABSTRACT

Disclosed is are the palmitate, stearate and 4-phenylbenzoate esters of D-γ-tocotrienol which are the only known derivatives of D-γ-tocotrienol which are crystalline solids and, therefore, may be utilized in the isolation and purification of D-γ-tocotrienol by crystallization and recrystallization procedures.

4 Claims, No Drawings

CRYSTALLINE TOCOTRIENOL ESTERS

This invention pertains to certain novel esters of D-γ-tocotrienol and, more particularly, to the palmitate, stearate and 4-phenylbenzoate esters of D-γ-tocotrienol. These esters are the only known derivatives of D-γ-tocotrienol which are crystalline solids. Thus, they are especially useful in the isolation and purification of D-γ-tocotrienol by crystallization and recrystallization procedures.

D-γ-tocotrienol is a substance which occurs naturally at very low concentrations in many plant tissues (J. Bauernfield in "Vitamin E, A Comprehensive Treatise", ed. L. Machlin, Marcel Dekker, New York, 1980, pp. 99–167). D-γ-Tocotrienol is reported to have several beneficial physiological effects in humans. These include antitumor activity [A. Kato et al, J. Jpn. Oil Chemists Soc. 34, 375 (1985); K. Komiyama et al., Chem. Pharm, Bull. 37, 1369 (1989)], antihypercholesterolemic activity [A. Qureshi et al., Am. J. Clin. Nutr. 53, 1021S (1991); T. Watkins et al, Lipids 28, 1113 (1993); D. Tan et al., Am. J. Clin. Nutr. 53, 1027S (1991); R. Parker et al., J. Biol. Chem. 268, 11230 (1993); J. Wright et al., European Patent Application 90119040.5 (1990) (EP421419 published Apr. 1, 1992); and J. Wright et al., U.S. Pat. No. 5,217,992 (1993)], and antioxidant activity [M. Yamaoka et al., J. Am. Oil Chemists Soc. 68, 114 (1991)]. Thus γ-tocotrienol is useful as a pharmaceutical material and as a nutritional supplement.

Since D-γ-tocotrienol occurs at very low levels in its natural sources, the concentration and isolation of the substance in pure form presents formidable difficulties. Thus, A. Kato et al. [(Jpn. Kokai Sho61-93178 (1986)] report the use of solvent partitioning, silica gel chromatography, and ion exchange chromatography to enrich the concentration of tocotrienols in rice bran oil deodorized fraction. These workers did not obtain a substantially pure D-γ-tocotrienol, however. British Patent Application GB 2 218 989 A (1989) claims the use of chromatography over alumina, silica gel, or activated carbon to concentrate mixed tocopherols and tocotrienols obtained from esterified palm oil. Again, pure D-γ-tocotrienol was not recovered.

U.S. Pat. No. 4,939,276 discloses the use of complexation with calcium hydroxide to increase the concentration of tocopherols and tocotrienols in a palm oil distillate from 1.1% to 38.5%. PCT International Publication No. WO 91/17985 discloses the recovery of a mixed tocopherol-tocotrienol fraction of around 2000 parts per million total tocols from rice bran and suggests the use of silica gel chromatography to further. enrich the material. U.S. Pat. No. 5,190,618 discloses the production of mixed tocopherol/tocotrienol concentrates from palm oil by a combination of distillation, ion exchange chromatography, and further molecular distillation. The product obtained contained up to 95% tocopherols and tocotrienols.

All of the above-described processes produce an oily fraction enriched in tocopherols and tocotrienols but do not actually produce the desirable D-γ-tocotrienol in a pure, homogeneous state. This is because D-γ-tocotrienol has a boiling point, solubility, and chromatographic mobility very close to those of the homologous series of other tocotrienols and the tocopherols as well. Thus the isolation of pure D-γ-tocotrienol remains a very difficult and expensive procedure, and no commercially useful method has been reported.

One of the most efficient and least expensive methods for purification of organic compounds is crystallization/recrystallization. Since D-γ-tocotrienol is an uncrystallizable oil, and heretofore no crystalline derivatives of the substance have been discovered, this technique has not been employed in this area. J. Baxter et al. [J. Am. Chem. Soc. 65, 918 (1943)] reported the preparation of the acid succinate, palmitate, para-azobenzene carboxylate, and allophantate esters of α-, β- and γ-tocopherol which were in some instances crystalline. The free tocopherols could be regenerated from these esters through saponification. These workers did not make any derivatives of the tocotrienols. It was noted in this work that there are no generally crystalline derivatives of the tocopherols. Thus while D-α-tocopheryl acid succinate is crystalline, the corresponding succinates of β- and γ-tocopherol did not crystallize. α- and γ-Tocopheryl palmitates, but not β-tocopheryl palmitate, crystallized. Therefore, one is not able a priori to predict whether any given ester of a compound in the tocopherol class will be crystalline.

I have discovered that the palmitate, stearate, and 4-phenylbenzoate esters of D-γ-tocotrienol are crystalline substances which can be used in the isolation of pure γ-tocotrienol from mixed tocopherol/tocotrienol sources. These three crystalline esters are novel composition of matter. Thus, a mixture containing D-γ-tocotrienol and other tocotrienols and/or tocopherols or other lipid substances can be esterified to form either the palmitate, stearate, or 4-phenylbenzoate ester of the tocotrienols and tocopherols present using commonly practiced esterification techniques. The D-γ-tocotrienyl ester is recovered in substantially pure form, i.e., 99+% pure, through repeated recrystallization from common solvents such as ethanol, isopropanol, or acetone. The substantially pure crystalline γ-tocotrienyl ester then may be saponified or hydrolysed using commonly practiced techniques to generate pure D-γ-tocotrienol.

The preparation and isolation of the novel crystalline esters of the present invention are further illustrated by the following examples.

EXAMPLE 1

Preparation of D-γ-tocotrienyl stearate: A solution of 5.0 grams of a palm oil concentrate consisting of about 90% mixed tocopherols and tocotrienols in a mixture of 20 mL of pyridine and 20 mL of dichloromethane was stirred under nitrogen at room temperature. Stearoyl chloride (3.65 grams) was added and the mixture stirred at room temperature for 24 hours. The reaction mixture then was poured into 400 of water, diluted with 75 mL of dichloromethane, and transferred to a separatory funnel. After shaking, the lower organic layer was recovered, washed with water, washed with. 5% aqueous HCl, washed with brine, dried over anhydrous sodium sulfate, and stripped of solvents on a rotary evaporator. The residual oily product was dissolved in about 25 mL of acetone and allowed to stand in the refrigerator for 24 hours. The resulting pale yellow crystals were filtered off and recrystallized twice from acetone to afford 4.8 grams of D-γ-tocotrienyl stearate as lovely white plates, m.p. 50°–52° C.

The material had mass spectrum m/e 676 (Calc., 676) and elemental analysis, Calc. for $C_{46}H_{76}O_3$, C, 81.6%, H, 11.3%. Found: C, 81.4%, H, 11.7%. The proton nmr spectrum together with these data show that the material is entirely D-γ-tocotrienyl stearate. The presence of stearates of other tocols was not detected.

Free D-γ-tocotrienol can be regenerated from the stearate ester by saponification in methanol according to the method described by J. Baxter et al., J. Am. Chem. Soc. 65, 918 (1943).

EXAMPLE 2

Example 1 was repeated using palmitoyl chloride to produce D-γ-tocotrienyl palmitate was prepared in the same fashion. Repeated recrystallizations from isopropanol and acetone gave substantially pure D-γ-tocotrienyl palmitate, m.p. 38°–42° C.

EXAMPLE 3

Example 1 was repeated using 4-phenylbenzoyl chloride and recrystallization from ethanol to produce crystalline D-γ-tocotrienyl 4-phenylbenzoate, m.p. 56°–60° C., mass spectrum m/e 590 (Calc, 590).

The invention has been described in detail with particular reference to preferred embodiments thereof, but it will be understood that variations and modifications can be effected within the spirit and scope of the invention.

I claim:

1. A crystalline ester of D-γ-tocotrienol selected from the group consisting of D-γ-tocotrienyl stearate, D-γ-tocotrienyl palmitate and D-γ-tocotrienyl 4-phenylbenzoate.

2. Crystalline D-γ-tocotrienyl stearate.

3. Crystalline D-γ-tocotrienyl palmitate.

4. Crystalline D-γ-tocotrienyl 4-phenylbenzoate.

* * * * *